United States Patent [19]

Gallucci

[11] Patent Number: 4,933,425
[45] Date of Patent: Jun. 12, 1990

[54] AROMATIC POLYCARBONATE CAPPED WITH NORBORNENE PHENYL IMIDE COMPOUND

[75] Inventor: Robert R. Gallucci, Mt. Vernon, Ind.

[73] Assignee: General Electric Co., Mt. Vernon, Ind.

[21] Appl. No.: 232,032

[22] Filed: Aug. 15, 1988

[51] Int. Cl.$^5$ .............................................. C08G 63/62
[52] U.S. Cl. ..................... 528/199; 525/462; 525/467; 525/468; 528/196; 528/198; 548/548
[58] Field of Search ....................... 528/199, 198, 196; 525/462, 467, 468

[56] References Cited

U.S. PATENT DOCUMENTS 4,645,822 2/1987 Stix et al. .
4,663,424 5/1987 Stix et al. .

OTHER PUBLICATIONS

CA105 173280F 1987.

Primary Examiner—Harold D. Anderson
Attorney, Agent, or Firm—Martin Barancik

[57] ABSTRACT

An aromatic polycarbonate containing at least one terminal group represented by the formula

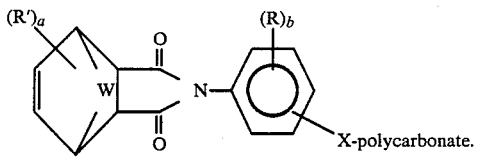

wherein R and R' are the same or different and are alkyl, aryl or halogen; a and b are the same or different and are zero or an integer of one to four; W is O, S, SO, $SO_2$, $CH_2$, CHR or $CR_2$ wherein R is identified above:

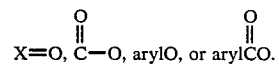

Preferably a and b are the same or different and are zero or one, more preferably each is zero. W is $CH_2$, CHR or $CR_2$.

8 Claims, No Drawings

AROMATIC POLYCARBONATE CAPPED WITH NORBORNENE PHENYL IMIDE COMPOUND

BACKGROUND OF THE INVENTION

The importance of endcapping or terminating polycarbonates with certain end or terminal groups is well known. Polycarbonates which are not so endcapped are generally insufficiently heat stable since the free phenolic end groups provide reactive sites which are generally detrimental to the thermal stability of the polycarbonate. Well known and conventionally used endcapping agents include phenol compounds such as paratertiary butyl phenol, Chroman-I, paracumylphenol, and phenol itself. The prior art also discloses other types of compounds that are effective endcapping agents for the carbonate polymers. These endcapping agents include the alkyl phenols disclosed in U.S. Pat. No. 4,269,964 and Japanese patent publication No. 34992/76; the alkenyl amines disclosed in U.S. Pat. No. 3,085,992; the amides disclosed in U.S. Pat. No. 3,399,172; aniline and methylaniline as disclosed in U.S. Pat. No. 3,275,601; and the primary and secondary amines disclosed in U.S. Pat. No. 4,001,184. Other endcapping agents described in the prior art include the aromatic amines disclosed in U.S. Pat. No. 3,028,365; and the ammonium compounds, ammonia, primary cycloalkyl amines, and primary aliphatic or alkyl amines disclosed in U.S. Pat. No. 4,111,910.

Various functionalized phenyl maleimides have been used to control polyamide molecular weight. These resins are claimed to be useful in ultraviolet cross-linkable compositions, see U.S. Pat. No. 4,645,822, assigned to Bayer. In existing maleimide capped resins, the highly reactive maleimide group is left exposed after isolation of resin. It is likely that many of the unsaturated end groups will react even before the polymer melts. In addition, the maleimide grouping is relatively toxic and therefore handling of the material is somewhat restrictive.

A novel material has been discovered which bypasses the above problems. A masked maleimide endcapped polycarbonate is prepared from the substituted phenolic chain capping material. This material is extremely stable and not abnormally toxic at room temperature. However, when heated to relatively high temperaures as in an extruder, the masking portion of the molecule is cleaved, therefore leaving the maleimide endcapped polycarbonate available for further reaction with itself or with other polymer systems thereby providing a new route to novel copolymers through a melt grafting process.

SUMMARY OF THE INVENTION

In accordance with the invention there is a polycarbonate containing at least one terminal group represented by the formula

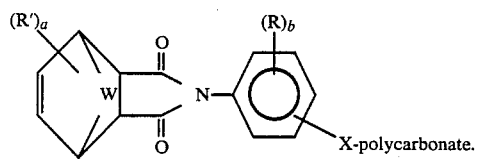

wherein R and R' are the same or different and are alkyl, aryl or halogen, a and b are the same or different and are zero or an integer of one to four. W is O, S, SO, SO$_2$, CH$_2$, CHR or CR$_2$ wherein R is identified above.

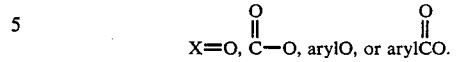

Preferably a and b are the same or different and are zero or one, more preferably each is zero. W is preferably CHR, CH$_2$ or CR$_2$.

Another aspect of the invention is a composition of the formula

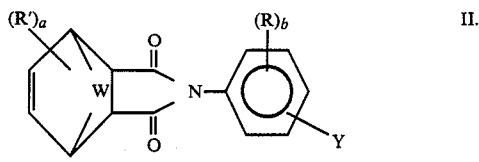

wherein R, R', a, b and W are as defined above. Y is OH; CR$_2^2$COOH wherein each R$^2$ is independent and hydrogen, alkyl of one to six carbon atoms, inclusive; COR$^3$ wherein R$^3$ is chloro, bromo or hydroxy; arylCOOH; or arylOH.

DETAILED DESCRIPTION OF THE INVENTION

Polycarbonates which can be endcapped with the novel phenolic chain terminating agent of Formula II may be conveniently prepared by a number of different well known conventional methods. One of these methods includes introducing an endcapping or chain terminating amount of at least one compound of Formula II into the polymer forming reaction as one of the reactants. These polycarbonate reactions are well known in the art and include such conventional processes as the interfacial polymerization reaction, the pyridine process, and melt polymerization. In general these reactions involve reacting at least (1) a dihydric phenol;
(2) a carbonate precursor; and
(3) an endcapping amount of at least one endcapping agent of Formula II.

The high molecular weight aromatic polycarbonate resins are well known compounds which are described along with methods for their preparation in interalia in U.S. Pat. Nos. 3,989,672; 3,275,601 and 3,028,365, all of which are incorporated herein by reference.

They may be conveniently prepared by the reaction of at least one dihydric phenol and a carbonate precursor. The dihydric phenols employed in the practice of this invention are known dihydric phenols which may be represented by the general formula

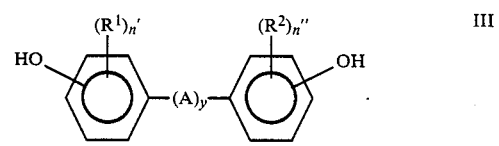

wherein:

R$^1$ is independently selected from halogen, monovalent hydrocarbon, and monovalent hydrocarbonoxy radicals;

$R^2$ is independently selected from halogen, monovalent hydrocarbon, and monovalent hydrocarbonoxy radicals;

A is selected from divalent hydrocarbon radicals,

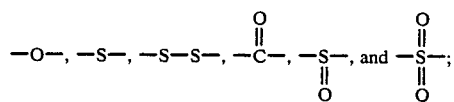

n' and n" are independently selected from integers having a value of from 0 to 4 inclusive; and y is either zero or one.

The monovalent hydrocarbon radicals represented by $R^1$ and $R^2$ include the alkyl, cycloalkyl, aryl, aralkyl, and alkaryl radicals.

The preferred alkyl radicals are those containing from 1 to about 12 carbon atoms. The preferred cycloalkyl radicals are those containing from 4 to about 8 ring carbon atoms. The preferred aryl radicals are those containing from 6 to 12 ring carbon atoms, i.e., phenyl, naphthyl, and biphenyl. The preferred aralkyl and alkaryl radicals are those containing from 7 to about 14 carbon atoms.

The preferred halogen radicals represented by $R^1$ and $R^2$ are chlorine and bromine.

The monovalent hydrocarbonoxy radicals may be represented by the general formula $-OR^3$ wherein $R^3$ has the same meaning as $R^1$ and $R^2$. The preferred hydrocarbonoxy radicals are the alkoxy and the aryloxy radicals.

The divalent hydrocarbon radicals represented by A include the alkylene, alkylidene, cycloalkylene, and cycloalkylidene radicals. The preferred alkylene radicals are those containing from 2 to about 30 carbon atoms. The preferred alkylidene radicals are those containing from 1 to about 30 carbon atoms. The preferred cycloalkylene and cycloalkylidene radicals are those containing from 6 to about 16 ring carbon atoms.

Some illustrative non-limiting of suitable dihydric phenols include:
2,2-bis(4-hydroxyphenyl)propane (bisphenol-A);
2,2-bis(3,5-dimethyl-4-hydroxyphenyl)propane;
2,2-bis(3,5-dibromo-4-hydroxyphenyl)propane;
1,1-bis(4-hydroxyphenyl)cyclohexane;
1,1-bis(3,5-dimethyl-4-hydroxyphenyl)cyclohexane;
1,1-bis(4-hydroxyphenyl)cyclododecane;
1,1-bis(4-hydroxyphenyl)decane;
1,4-bis(4-hydroxyphenyl)butane;
p,p'-dihydroxydiphenyl;
bis(4-hydroxyphenyl)ether; and
4,4'-thiodiphenol.

Other useful dihydric phenols are descrfibed, inter alia, in U.S. Pat. Nos. 3,028,365; 2,999,835; 3,148,172; 3,271,368; 2,991,273; 3,271,367; 3,280,078; 3,014,891 and 2,999,846, all of which are incorporated herein by reference.

The carbonate precursors employed in the practice of the instant invention include the carbonyl halides, the bishaloformates, and the diarylcarbonates. The carbonyl halides include carbonyl bromide, carbonyl chloride, and mixtures thereof. Typical of the diarylcarbonates are diphenyl carbonate; di(halophenyl) carbonates such as di(chlorophenyl)carbonate, di(bromophenyl) carbonate, di(trichlorophenyl)carbonate, and di(tribromophenyl)carbonate; di(alkylphenyl)carbonates such as di(tolyl)carbonate; dinaphthyl carbonate; di(halonaphthyl)carbonates; and naphthyl phenyl carbonate. The bishaloformates suitable for use herein include the bishaloformates of dihydric phenols such as the bischloroformates of hydroquinone and bisphenol-A; the bishaloformates of glycols such as the bischloroformates of ethylene glycol, neopentyl glycol, and polyethylene glycol.

The polycarbonates of the instant invention contain at least one recurring structural unit represented by the formula

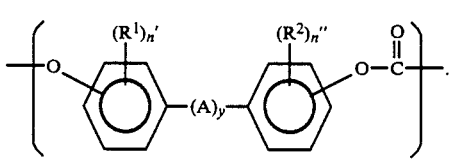

wherein A, $R^1$, $R^2$, n', n" and y are as defined hereinafore.

The polycarbonates of the instant invention also contain terminal or end groups represented by the general formula

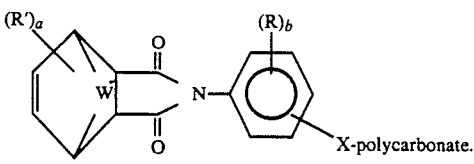

wherein R, R', a, b, W and X are as defined hereinafore.

In a preferred embodiment the instant polymers will contain two moles of end groups of Formula II per mole of carbonate polymer.

The instant polycarbonates are high molecular weight aromatic carbonate polymers having an intrinsic viscosity, as determined in chloroform at 25° C. of from about 0.3 to about 1.5 dl/gm, preferably from about 0.45 to about 1.0 dl/gm. These polycarbonate generally have a weight average molecular weight of from about 10,000 to about 200,000, preferably from about 20,000 to about 100,000 as measured by gel permeation chromatography.

Another embodiment of the instant invention involves using the endcapping agents of Formula II in conjunction with the conventional known endcapping or chain terminating agents such as Chroman I, phenol, and p-tertiarybutylphenol. In such case a statistical mixture of polymers containing different terminal groups will be formed. The amounts of the various terminal groups present will depend on the relative amounts and relative reactivities of the various chain terminating agents used.

Also included with the scope of the instant invention are the high molecular weight thermoplastic randomly branched polycarbonates. These randomly branched polycarbonates may be prepared by utilizing a minor amount of a branching agent. These branching agents are well known in the art and are generally organic polyfunctional aromatic compounds containing at least three functional groups which may be hydroxyl, carboxyl, carboxylic anhydride, haloformyl and mixtures thereof. Some illustrative non-limiting examples of these branching agents include trimellitic anhydride, trimetallic acid, trimellityl trichloride, 4-chloroformyl phthalic anhydride, pyrommellitic acid, pyromellitic dianhydride, trimesic acid, and benzophenonetetra carboxylic acid. Some other useful branching agents are disclosed in U.S. Pat. Nos. 3,635,895; 4,001,184 and 4,204,047, all of which are incorporated herein by reference.

A convenient method of preparing the instant polycarbonate is the interfacial polymerization process. This process involves the coreaction of (i) at least one dihydric phenol, (ii) a carbonate precursor such as phosgene, and (iii) an endcapping amount, i.e., from about 0.1 to about 10 mole percent, based on the moles of dihydric phenol used, of at least one endcapping agent of Formula II. The reaction is carried out in the presence of two different liquid phases which are immiscible with each other and which constitute two solvent media. Normally one of these liquid phases is an alkaline aqueous medium while the other liquid phase is an organic medium such as methylene chloride. Also present are catalysts which are conventionally used in the interfacial polymerization process of forming polycarbonates. These catalysts include, but are not limited to, tertiary amines such as triethylamine, quaternary ammonium compounds, and quaternary phosphonium compounds.

Also included within the scope of the instant invention are the copolyestercarbonate resins which are described, inter alia, in U.S. Pat. Nos. 3,169,121 and 4,465,820, which are incorporated herein by reference. These copolyestercarbonates may be prepared by reacting (i) at least one dihydric phenol, (ii) a carbonate precursor, (iii) at least one compound of Formula II, and (iv) at least one ester precursor.

The carbonate polymers of the instant invention may optionally have admixed therewith the commonly known and used additives such as antioxidants, inert fillers such as clay, mica, talc, and glass; impact modifiers; ultraviolet radiation absorbers such as benzophenones; hydrolytic stabilizers such as the epoxides taught in U.S. Pat. Nos. 3,489,716; 4,138, 379 and 3,839,247, all of which are incorporated herein by reference; color stabilizers such as the organophosphites disclosed in U.S. Pat. Nos. 3,305,520 and 4,118,370, both of which are incorporated herein by reference; and flame retardant agents.

At least one of the chain terminating agents is a compound of Formula II. The compound of Formula II is prepared by the simple imidization as shown below wherein the compound of Formula V is reacted with the compound of Formula VI.

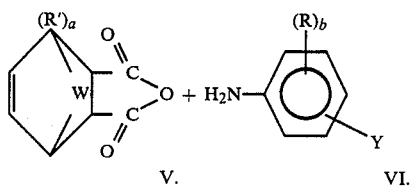

wherein R, R', a, b and Y are as previously defined.

The amine phenols or amine carboxylic acids or derivatives and substituted molecules of Formula VI are well known in the art. The compounds of Formula V are simply prepared by the Diels-Alder diene dienophile adduct reaction between compounds of Formula VII and Formula VIII shown below.

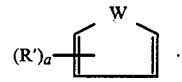

wherein W, R' and a are as defined above. Preferably W is CHR or $CR^2$, R" is chloro or alkyl of one to three carbon atoms, inclusive, and a is zero or one, more preferably one. The compound of Formula VIII, a cyclic -B unsaturated carboxylic acid anhydride such as maleic anhydride, is below.

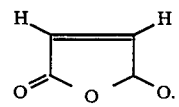

An alternative reaction scheme is to react the compound of Formula VIII with the compound of Formula VI to form the imide which is then reacted with the compound of Formula VII to form the compound of Formula II. As used above and in the claims, alkyl is normal or branched hydrocarbon of one to six carbon atoms, inclusive, aryl is phenyl or napthyl and halogen is fluoro, chloro or bormo.

The compound of Formula II is then used as a chain terminating agent in the usual preparation of polycarbonate as one of ordinary skill in the art would use any phenol such as phenol or paratertiary butyl phenol. In general the chain terminating agent of Formula II should be present in from about 1.0 to about 10.0 mole percent based upon the moles of the dihydric phenol present in the polycarbonate.

The finally prepared polycarbonate endcap with the compound of Formula II is non-toxic, easy to handle, and is non-reactive at ordinary temperatures. However, at temperatures of about 250° to about 350° C., the norbornene like portion of the compound becomes labile and is lost from the molecule as cyclic diene, thereby leaving a maleimide end group, shown below

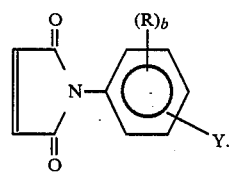

wherein R, b and Y are hereinafore defined. Such a temperature is commonly achieved during extrusion of the polycarbonate. Therefore during extrusion processes the chain terminated polycarbonate of this invention becomes reactive and can react with itself or with other materials providing reactive sites for the maleimide. Examples of such materials include polyolefins and styrenic molecules such as acrylonitrile, butadiene-styrenes. Under these circumstances, new copolymers will be formed from the covalent reactions which occur between the maleimide and the active site of the other polymer.

Below are examples of the invention. These examples are intended to illustrate rather than narrow the general inventive concept of the invention.

EXAMPLE 1

Preparation of Norbornene-Hydroxy Phenol Imides a. Norbornene dicarboxylic anhydride, 180 g (1.1 m) was dissolved in 250 ml chlorobenzene in a flask fitted with a mechanical stirrer and an apparatus to remove water. m-Amino phenol, 120.0 g (1.1 m) was added to the solution with stirring. Dimethylamino pyridine (1.0 g) was added as catalyst. The reaction was heated to reflux under nitrogen with removal of 20 ml water, and 50 ml solvent. The reaction was then cooled to 40° C. The product crystallized from solution and was isolated by hot filtration. The crude product was washed with isopropanol. Yield 262.5 g, 94%, of a tan crystalline product. A second crop of darker orange solid, 5.2 g, was discarded. mp 194°–208° C. (DSC peak at 200° C.). IR(KBr) 3380, 1760, 1690, 1610, 1460, 1390, 1270, 1180 cm$^{-1}$. CNMR 176.8, 157.2, 134.4, 128.1, 123.5, 115.3, 51.6, 45.2, 44.8, ppm d$_6$-DMSO.

b. The adduct of p-amino phenol and norbornene dicarboxylic anhydride was prepared in a similar fashion yielding 91% of a fluffy powder, mp 245°–249° C. IR(KBr) 3380, 1770, 1690, 1520, 1390, 1280, 1180 cm$^{-1}$. CNMR 176.5, 157.7, 134.4, 133.3, 129.4, 117.6, 115.3, 114.2, 51.7, 45.3, 44.8, ppm d$_6$-DMSO.

The norbornene imides were insoluble in methylene chloride, water and acetic acid and soluble in sodium hydroxide and hot isopropanol. Materials were used in polymerization with no further purification.

EXAMPLE 2

A representative polymerization is described below. A five necked resin kettle was charged with 2.0 L methylene chloride, 1.5 L deionized water, 500 g (2.19 m) bisphenol-A, 13.9 (0.055 m) m-amino phenol norbornene imide from Example 1a and 3.0 ml triethylamine. The solution was phosgenated at 2.0 g/min for 2 hr. pH 9.5–10.5 was maintained by addition of 50% aqueous NaOH. After phosgenation the crude aqueous layer showed no precipitate upon acidification. The organic layer was washed once with water, once with 5% aqueous HCL and 3 times again with water. Polymer was isolated by addition to steam heated water in a large blender. All intrinsic viscosities (IV) were measured in chloroform. GPC results are relative to polystyrene standards.

TABLE I

IMIDE PHENOL CAPPED POLYCARBONATES

| SAMPLE | MOLE % PHENOL* END-CAPPER | Mw | Mn | DISP | IV dl/g | Tg °C. |
|---|---|---|---|---|---|---|
| A | 1.0 | 122800 | 44200 | 2.8 | 0.846 | 156 |
| B | 1.6 | 67900 | 28000 | 2.4 | 0.644 | 154 |
| C | 2.5 | 79000 | 20300 | 3.9 | 0.711 | 152 |
| D | 2.5 | 66300 | 20000 | 3.3 | 0.699 | 153 |
| E | 2.5 | 74700 | 22200 | 3.4 | 0.699 | 153 |

*Mole % based on BPA

In most cases GPC analysis of these polymers showed a wide polydispersity due to a low molecular weight tail. However comparison of a hot water, methanol or acetone precipitated polymer showed similar imide content. The polymers formed a tough flexible transparent film from methylene chloride solution.

EXAMPLE 3

Combined samples C, D and E were heated at 260° C., 32 rpm for 20 minutes in a steel mixing bowl. The fluffy powder took 13 minutes to load into the mixing bowl.

| TIME, MINUTES (AFTER LOADING) | IV dl/g (CHCl3) at 25° C. |
|---|---|
| 1 | 0.708 |
| 3 | 0.710 |
| 5 | 0.705 |
| 10 | 0.714 |
| 15 | 0.714 |
| 20 | 0.735 |

The increase in I.V. demonstrates that the polymers are losing cyclopentadiene and crosslinking at the maleimide bond.

EXAMPLE 4 a. Reaction was similar to a standard interfacial polymerization with 200 ml methylene chloride, 300 ml deionized water, 12.5 g bisphenol-A (0.061 m), 7.0 g norborne parahydroxy phenolimide from Example 1b (0.0276 m) and 0.5 ml triethylamine. COCl$_2$ was added at 1.0 g/min for 14 minutes at pH 10–11. After separation from the water layer the methylene chloride layer was washed once with water, once with 5% HCL and four times with water. The solution was dried over anhydrous potassium carbonate and evaporated to dryness. Yield 17.2 g. IR spectra showed very little hydroxy absorbance, carbonyl region showed peaks at 1770, 1715 cm$^{-1}$. IV=0.175 dl/g, Tg 101°·C., CNMR 176.3, 151.5, 150.5, 148.6, 148.1, 134.5, 133.2, 129.7, 127.7, 125.1, 120.9, 120.6, 119.9, 51.7 45.5, 44.9, 42.1, 30.4 ppm d$_6$-DMSO.

The polymer showed 30 wt. % imide end groups (83% incorporation). Imide end group incorporation was also confirmed by carbon-13 NMR.

Analysis of the polymer by thermal gravimetric analysis (TGA) showed a weight loss of 6.9% between 260°–360° C. This weight loss corresponds to the loss of cyclopentadiene liberating the reactive maleimide end group.

b. The meta phenol imide of Example 1a was used to prepare oligomers by a similar route as above using 5.0 g m-phenolimide (0.02 m) and 8.9 g BPA (0.039 m). Yield 13.5 g. IR spectra was as above. CNMR 176.5, 150.0, 148.6, 148.2, 148.1, 134.5, 130.2, 128.3, 127.7, 121.7, 120.6, 51.7, 45.4, 44.8, 42.1, 30.4 ppm d$_6$-DMSO. IV=0.108 dl/g, Tg 108° C.

The polymer showed 32 wt. % imide end groups (89% incorporation). Imide phenol end group incorporation was confirmed by carbon-13 NMR.

TGA analysis showed an 8.4% weight loss between 260°–360° C. (Theoretical weight loss of cyclopentadiene 8.9%).

What is claimed is:

1. An aromatic polycarbonate containing at least one terminal group represented by the formula

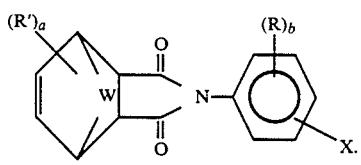

wherein R and R' are the same or different and are alkyl, aryl or halogen; a and b are the same or different and are zero or an integer of one to four; W is O, S, SO, SO$_2$, CH$_2$, CHR or CR$^2$ wherein R is identified above;

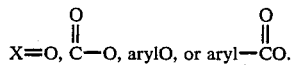
X=O, C—O, arylO, or aryl—CO.

2. The polycarbonate of claim 1 wherein b is zero.

3. The polycarbonate of claim 1 wherein a is zero.
4. The polycarbonate of claim 1 wherein X is oxygen.
5. The polycarbonate of claim 1 wherein W is CHR, CH$_2$ or CR$_2$.
6. The polycarbonate of claim 5 wherein X is O and a and b are each zero.
7. The polycarbonate of claim 6 wherein W is CH$_2$ and X is meta to the nitrogen group.
8. The polycarbonate of claim 6 wherein W is CH$_2$ and X is para to the nitrogen group.

* * * * *